United States Patent [19]

Widlund et al.

[11] 4,222,381
[45] Sep. 16, 1980

[54] MENSTRUAL TAMPON

[75] Inventors: Leif U. R. Widlund; Kerstin A. H. Strandberg, both of Mölnlycke, Sweden

[73] Assignee: Molnlycke AB, Molnlycke, Sweden

[21] Appl. No.: 971,012

[22] Filed: Dec. 15, 1978

[30] Foreign Application Priority Data

Dec. 21, 1977 [SE] Sweden ............................... 7714598

[51] Int. Cl.³ ............................................. A61F 13/20
[52] U.S. Cl. ..................................... 128/270; 128/285
[58] Field of Search ............................... 128/270, 285; 28/118-120

[56] References Cited

U.S. PATENT DOCUMENTS

| 2,112,021 | 3/1938 | Harris | 128/285 |
| 2,286,817 | 0/1942 | Knight | 28/120 |
| 3,814,469 | 6/1974 | Simon | 28/120 |
| 3,845,767 | 11/1974 | Friese et al. | 128/285 |
| 3,854,481 | 12/1974 | Messing | 128/285 |

FOREIGN PATENT DOCUMENTS

| 128793 | of 1948 | Australia | 128/285 |
| 808851 | of 1969 | Canada | 128/285 |
| 2114529 | of 1972 | Fed. Rep. of Germany . | |
| 1007643 | of 1952 | France . | |
| 2229384 | of 1974 | France . | |
| 143068 | of 1953 | Sweden . | |
| 7203871 | of 1977 | Sweden . | |
| 7704412 | 1/1977 | Sweden | 128/285 |
| 324888 | of 1957 | Switzerland | 128/285 |
| 490024 | of 1938 | United Kingdom . | |

Primary Examiner—William E. Kamm
Assistant Examiner—C. W. Shedd
Attorney, Agent, or Firm—Young & Thompson

[57] ABSTRACT

In a menstrual tampon comprising one or more webs 1, rolled up in several layers around each other, of moisture-absorbing material, a pull string 2 is anchored and extends out of the tampon. This string is laid around the web 1 in at least two consecutive loops which, with portions 6 running back and forth approximately longitudinally to the tampon, surround and are in contact with at least two opposite side edges 7,8 of the web 1 of absorbent material, and extend out of one end of the tampon. (FIG. 2).

8 Claims, 6 Drawing Figures

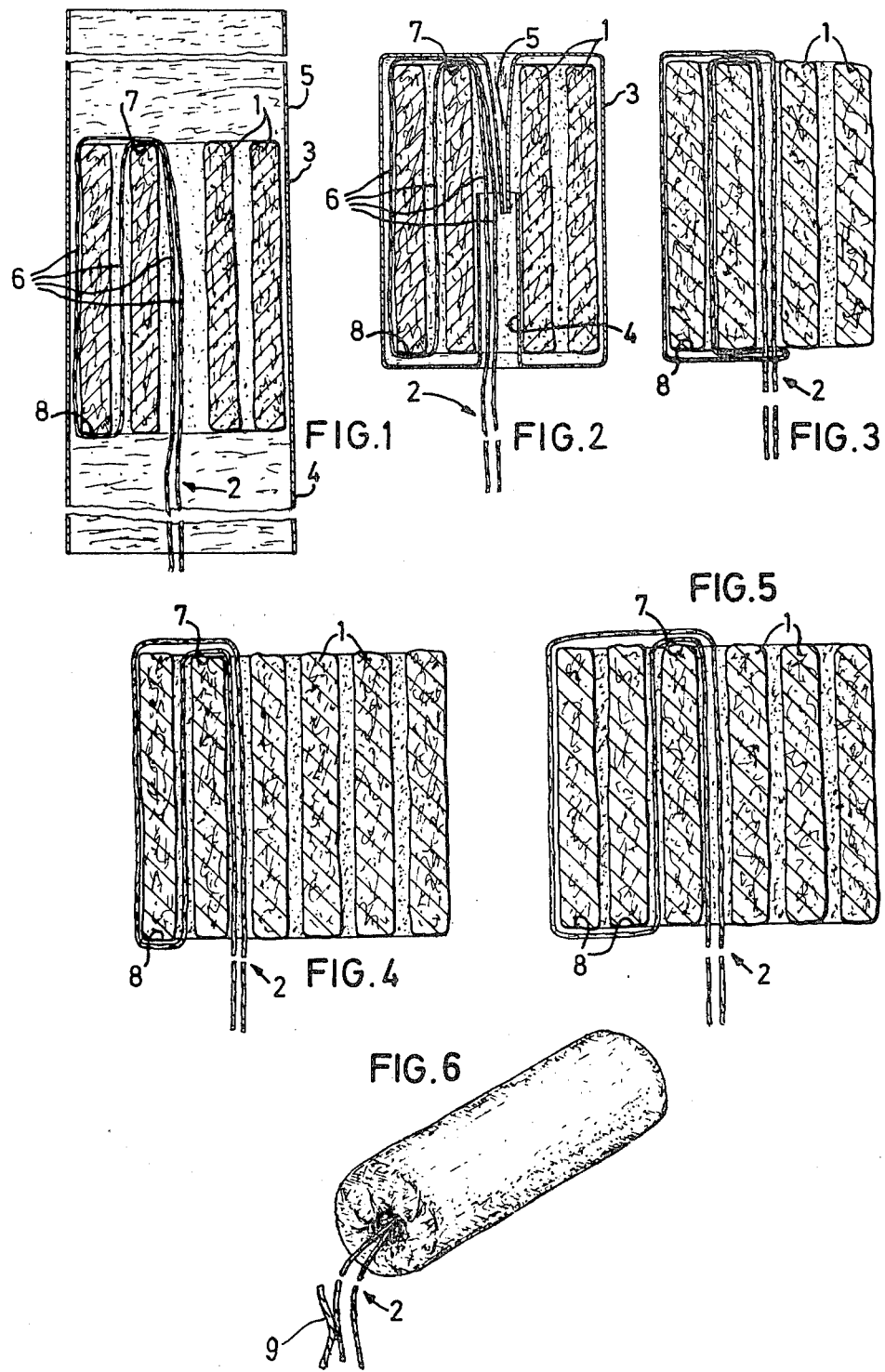

MENSTRUAL TAMPON

The present invention relates to a menstrual tampon of the type which comprises at least one web, rolled up in several layers around each other, of moisture absorbing material, in which web a pull string for removing the tampon from the vagina is anchored and extends out of the tampon.

Tampons of this type have been known for many years, for example by British Pat. No. 490,024 of 1938. In order to assure that the pull string, laid in a single loop transversely around the absorbent material web in these tampons, would fulfill its function, one was forced to tie together the two ends of the pull string coming out of the tampon, so that the string would not by mistake be pulled out of a tampon in use, creating problems in removing the tampon after use.

Another example is the menstrual tampon disclosed in French Pat. No. 1,007,643 of 1952, whose pull string consists of a band sewn to two webs of absorbent material rolled onto one another.

Another example of anchoring of the pull string is shown in German Pat. No. 2,114,529, in which the string is shown laid in a single slipknot around the web of absorbent material in a menstrual tampon.

All of these anchoring methods have, however, involved an undesirable complication of the process as well as of the apparatus for producing the tampons.

Furthermore, the known anchorings of the string have had another substantial disadvantage in connection with the removal of the tampon from the vagina. Since the string is anchored in only one of the rolled layers of the tampon, there is a great risk that this layer will slide in relation to the surrounding layers when the tampon is removed by means of the string, so that the tampon is pulled apart through telescoping of the coiled layers, an occurance which is called in the following "spiraling". This has been especially prevalent in tampons wound of several layers of absorbent material with varying friction and binding characteristics.

A solution to the problem of spiraling of menstrual tampons is proposed in Swedish Pat. Application 7704412-1. A tampon is described of the type described in the introduction, in which a first portion of the pull string extends along the major portion of the total length of the web of absorbent material on or beneath the web along its length, while a second portion of the pull string is laid approximately perpendicularly to the length of the web of absorbent material out over one side edge of the web, the web being rolled starting at the end opposite to the bent end of the string, so that said end of the string exits approximately from the middle of the rolled tampon. The pull string is thus anchored against slipping out and it snares the swollen tampon when it is removed from the vagina as a result of the tractive and frictional forces. It is true that the tieing up of the roll facilitates the removal of the tampon from the vagina, at the same time as spiraling of the tampon (i.e. uncoiling of the web of absorbent material) cannot occur farther than to the place where the pull string is bent and goes through the mid-portion of the tampon. These advantages are, however, counterbalanced by the disadvantage that a tampon of the suggested type must contain an unnecessarily large number of coils (6-9 layers). Furthermore, it is doubtful that the electrostatic process disclosed for applying the string is simpler than other known processes for the application of pull strings in vaginal tampons.

The present invention has the purpose in connection with menstrual tampons of the type described in the introduction of achieving a new and improved anchoring of the pull string in the absorbent material. This anchoring should make tieing together of the string ends coming out of the tampons unnecessary and yet effectively hold the pull string in the tampons. Furthermore, it is capable of locking the layers of absorbent material in the tampons in relation to one another, effectively preventing spiraling of the tampons when removing them from the vagina, even in tampons made of a very few layers. Finally, the anchoring is so simple so as not to make the production of the tampons unnecessarily difficult.

Practical tests with a number of tampons made according to the invention have demonstrated that these advantages are achieved in all essential respects by virtue of the fact that the pull string in the tampons is, according to the invention, laid around the web of absorbent material in at least two consecutive loops which, with portions running back and forth approximately longitudinally to the tampon, surround and are in contact with at least two opposite side edges of the web of absorbent material, and extend out of one end of the tampon.

In addition to the fact that the invention achieves the desired new and improved anchoring of the pull string in the absorbent material, thus avoiding the need in a number of previously known tampons of tieing together of the string ends coming out of the tampon, it prevents in an effective manner all spiraling of the tampons by virtue of the fact that the new string anchoring locks the different layers in the web of absorbent material in relation to one another. Furthermore, the invention also has other important advantages in relation to the prior art. It simplifies the method as well as the apparatus for manufacturing the tampons by eliminating string tieing, sewing etc, and the complicated apparatus required for these steps can be eliminated. The placement of the pull string according to the invention in the tampon can be done with very simple and reliable means.

Within the scope of the invention, the pull string can be placed in loops around the web of absorbent material in several different ways. For example, it can be laid in two consecutive loops around a single or around several rolled layers of the web of absorbent material. In the former case, the pull string is in contact with both of the opposide side edges of the single web layer, and in the latter case it is in contact with all of the side edges of the web layers encircled by the string. In an especially suitable embodiment of the invention because it provides very good mutual locking of a plurality of rolled layers of the web, the pull string is laid in a loop around at least the outermost roll layer of the web of absorbent material in surrounding contact with the material web side edge which faces towards the end of the tampon out of which the ends of the string come, and in another loop around at least the innermost coil layer in surrounding contact with the material web side edge which faces away from said end of the tampon.

If the pull string in a tampon according to the invention comes out with both its ends from the center of the tampon and inside the innermost layer of the web of absorbent material, the significant advantage is achieved that at least a nearly axial removal of the tampon from the vagina is made possible.

The ends of the pull string can also pass through the loop which surrounds the side edge(s) of the layers of the web of absorbtion material which are directed towards the end of the tampon out of which the ends of the string come. This provides the advantage that the string is anchored to itself as well as to the rolled layers of the web of absorbent material.

In a tampon according to the invention, the ends of the pull string can either be free or joined to one another by, for example, tieing together, fusing together, gluing or the like.

The known menstrual tampons mentioned above all relate to fiber tampons without sheaths. Such tampons have the disadvantage, however, of losing fibers to a certain extent especially when a small amount of fluid is absorbed, since their surface fibers have a tendency to stick to the mucous membrane of the vagina, and thus also make the removal of the tampon more difficult. This disadvantage can, however, be obviated by providing the fiber tampons with a sheath of suitable material such as non-woven textile (with or without a binder between the fibers), a gauze weave, a knitted net or the like. A tampon provided with such a sheath is disclosed for example by Swedish Pat. No. 143,068 of 1953.

In previously known tampons, however, difficulties have arisen in combining the traditional string fastenings and the sheaths. Instead of leading the free ends of the string, which is fixed in the absorbent material, out through the sheath, so that they can serve as pull strings for the tampon, up to now manufacturers have chosen to attach the pull strings to the sheath itself. This has required apparatuses for sealing the sheaths and for attaching the pull strings, which has made the process of manufacture more complicated and significantly increased the cost of these tampons.

The new and improved anchoring of the pull string in a tampon according to the invention, however, provides the additional advantage in comparison with previously known attachment methods, that in those embodiments where both string ends exit from the center of the tampon and inside the innermost layer of the web of absorbent material, the anchoring does not present any obstacle to the application of a sheath, in spite of the fact that the string is securely anchored in the absorbent material, which was previously not possible. In a menstrual tampon according to the invention, a sheath can enclose the layers of absorbent material in the tampon and be folded into the center of the layers of absorbent material and the tampon. To facilitate the manufacture of the tampon, the sheath can be fixed to the absorbent material.

A tampon according to the invention is, after rolling up of the component materials and the application of the pull string, compressed in a manner known per se, so that it can be inserted into the vagina and so that the absorbent material remains unexpanded when dry but expands when moistened.

The invention will be described in more detail in the following with reference to several suitable embodiments shown in the accompanying drawings, of a menstrual tampon made according to the invention.

FIGS. 1 and 2 show two axial sections through one of these embodiments in which the absorbent material of the tampon is enclosed in a sheath, which in FIG. 1 is shown with freely extending ends and in FIG. 2 with its ends folded into the center of the layers of absorbent material and the tampon.

FIGS. 3, 4 and 5 show, on the other hand, in axial section, three additional embodiments in which the pull string of the tampon is laid around the layers of absorbent material in different manners.

FIG. 6 shows a perspective view of the tampon shown in FIGS. 1 and 2, in finished form ready for use.

As can be seen from FIGS. 1-5 in the drawing, a tampon according to the invention comprises at least one web 1 of a moisture absorbent material, rolled up in several layers, suitably consisting of one or more layers of highly absorbent fibers laid on top of one another, such as cellulose fibers or the like. This web has a breadth which corresponds to the length of the tampon and should be sufficiently long to be able to be rolled into at least two coils.

FIGS. 1-5, showing axial sections through tampons in their uncompressed state, also show how a pull string 2 for removal of the tampon from the vagina after use is anchored in the rolled web of absorbent material 1 with two string ends coming from one end of the tampon to be grasped by the fingers. The material in the string can be any suitable natural or synthetic material, which does not tend to untwine when made into a string. According to the invention, the pull string 2, with its two ends coming out of the tampon, is anchored in the web 1 of absorbent material in at least two consecutive loops which, with portions 6 running back and forth approximately longitudinally to the tampon, surround and are in contact with at least two opposite side edges 7,8 of the web 1 of absorbent material before the string extends with its ends out of one end of the tampon. As can be seen from FIGS. 1 and 2, the pull string 2 in the embodiment shown in these figures is laid in a loop around the outer layer of the web 1 of absorbent material, surrounding and in contact with the web side edge 8 which faces the end of the tampon from which the string ends extend, while the string runs in another loop around the inner layer surrounding and in contact with the web side edge 7 which faces away from said end of the tampon. The two string ends exit together from the center of the tampon and inside the innermost layer of the same.

In the embodiment shown in FIG. 3, the ends of the pull string 2 extend through the loop which surrounds the web layer side edge(s) 8 which face the end of the tampon from which the string ends extend.

In the embodiment shown in FIG. 4, the pull string 2 is laid in a loop around the outermost layer of the web 1 of absorbent material, in surrounding contact with the web side edge 8 which is facing the end of the tampon from which the string ends extend, and in another loop around the next-to-the-outermost layer in surrounding contact with the web side edge 7 which faces away from said end of the tampon.

In the embodiment shown in FIG. 5, however, the pull string 2 is laid in a loop around the two outermost layers of the web 1 of absorbent material in surrounding contact with the web side edges which face the end of the tampon out of which the string ends come, and in another loop around the inner layer in surrounding contact with the side edge 7 of the same which faces away from the previously mentioned end of the tampon.

In all of the embodiments shown in the drawing for a menstrual tampon according to the invention, the ends of the pull string are free. They can, of course, also be joined to one another by tieing, fusing, gluing or the like, as shown at 9 in FIG. 6.

As is evident from the embodiment shown in FIGS. 1 and 2, for a tampon according to the invention, a sheath 3 of suitable material can be placed around the coiled absorbent material 1 in the tampon. The sheath can suitably consist of a non-woven textile (with or without binder between the fibers), a gauze weave, a knitted net or the like. It is also possible for the sheath material 3 to be fastened at one end to the web 1 of absorbent material. This fastening can be achieved by means of a line of glue, a heat-pressure seal or the like, depending on the type of material. When the rolled web of absorbent material 1 is covered by at least one layer of sheath material 3 rolled around the same, the side edges 4,5 of sheath material extending at the ends of the tampon are folded into the center of the layers of absorbent material in the roll or tampon. Thus the roll of absorbent material is completely enclosed in the sheath 3, as shown in FIGS. 2 and 6.

To give the tampons the correct size and condition for insertion into the vagina, the rolled tampons, as shown in FIGS. 1 and 2, as well as in FIGS. 3, 4 and 5, with the pull string 2 anchored therein, are compressed in a manner known per se, so that the absorbent material in them remains unexpanded when dry but swells when wetted in the vagina. The tampon shown in FIGS. 1 and 2 after compression is shown in FIG. 6.

The invention is not limited to the embodiments described here and shown in the drawing, but can be modified in many ways within the scope of the appended claims.

What we claim is:

1. A menstrual tampon, comprising at least one web of moisture absorbing material which is rolled up to form several layers, the web having a pull string anchored therein for removing the tampon from the vagina and having ends extending from one end of the tampon, the pull string having a portion extending in a single loop on both sides of at least one of the layers of the absorbing material web and surrounding that side edge of the absorbing material web which is directed toward said end of the tampon from which said ends of the pull string extend, the two string portions which extend from the said loop at the opposite end of the tampon being laid over the side edge of at least one other layer of the absorbent material web situated inside the first-mentioned at least one layer or absorbent material and extending along the side of the said other layer and out said one end of the tampon.

2. A tampon as claimed in claim 1, wherein the pull string exits with both of its ends from the center of the tampon and from inside the innermost layer of the web of absorbent material.

3. A tampon as claimed in claim 1, wherein the ends of the pull string pass through the loop of said string which surrounds the side edge of the web layer which faces the end of the tampon from which the ends of the pull string emerge.

4. A tampon as claimed in claim 1, wherein the ends of the pull string are free.

5. A tampon as claimed in claim 1, wherein the ends of the pull string are joined together.

6. A tampon as claimed in claim 1, and a sheath which encloses the layers of absorbent material of the tampon and is folded into the center of the layers of absorbent material and the tampon.

7. A tampon as claimed in claim 6, wherein the tampon sheath is fastened to the absorbent material.

8. A tampon as claimed in claim 1, which is compressed to such a size and condition as to be insertable into the vagina.

* * * * *